(12) United States Patent
Nakamura et al.

(10) Patent No.: US 10,426,324 B2
(45) Date of Patent: Oct. 1, 2019

(54) IMAGING APPARATUS INCLUDING AN IMAGE SENSOR CHIP MOUNT ASSEMBLY

(71) Applicant: OLYMPUS CORPORATION, Tokyo (JP)

(72) Inventors: Mikio Nakamura, Tokyo (JP); Takanori Sekido, Machida (JP); Nau Satake, Yokohama (JP)

(73) Assignee: Olympus Corporation, Tokyo (JP)

( * ) Notice: Subject to any disclaimer, the term of this patent is extended or adjusted under 35 U.S.C. 154(b) by 279 days.

(21) Appl. No.: 15/268,947

(22) Filed: Sep. 19, 2016

(65) Prior Publication Data

US 2017/0000321 A1 Jan. 5, 2017

Related U.S. Application Data

(63) Continuation of application No. PCT/JP2015/058345, filed on Mar. 19, 2015.

(30) Foreign Application Priority Data

Mar. 20, 2014 (JP) ................................ 2014-059188
Jan. 13, 2015 (JP) ................................ 2015-004487

(51) Int. Cl.
*A61B 1/05* (2006.01)
*H01L 23/31* (2006.01)
(Continued)

(52) U.S. Cl.
CPC .............. *A61B 1/04* (2013.01); *A61B 1/0011* (2013.01); *A61B 1/051* (2013.01); *B23K 1/0016* (2013.01);
(Continued)

(58) Field of Classification Search
CPC ........................ A61B 1/05; A61B 1/04; A61B 1/0011; A61B 1/051; H04N 5/2254; H04N 5/2253;
(Continued)

(56) References Cited

U.S. PATENT DOCUMENTS

2006/0109368 A1* 5/2006 Ayrenschmalz ..... A61B 1/0011
                                                        348/340
2012/0206583 A1    8/2012 Hoshi et al.
(Continued)

FOREIGN PATENT DOCUMENTS

JP    H04-035474 A    2/1992
JP    H10-270144 A    10/1998
(Continued)

OTHER PUBLICATIONS

Japanese Office Action dated Sep. 18, 2018 in Japanese Patent Application No. 2016-508810.
(Continued)

*Primary Examiner* — John P Leubecker
(74) *Attorney, Agent, or Firm* — Scully Scott Murphy & Presser, P.C.

(57) ABSTRACT

An imaging apparatus mount assembly for an image sensor chip includes a substrate, a plurality of first pins and at least one first electronic component, both mounted on a first surface of the substrate, and a first resin sealant configured to seal the first surface so as to expose an end face of a first shaft section opposite to where a first connecting section is provided. A plurality of second pins and at least one second electronic component are both mounted on a second surface of the substrate. A second resin sealant is configured to seal the second surface so as to expose an end face of a second shaft section opposite to where a second connecting section is provided. The image sensor chip includes a light receiving unit and a back-surface electrode, the first shaft section exposed on the first resin sealant is connected to the back-surface electrode.

4 Claims, 14 Drawing Sheets

(51) Int. Cl.

| | |
|---|---|
| *H01L 27/146* | (2006.01) |
| *A61B 1/04* | (2006.01) |
| *H01L 21/56* | (2006.01) |
| *B23K 1/00* | (2006.01) |
| *B23K 3/06* | (2006.01) |
| *H01L 25/10* | (2006.01) |
| *A61B 1/00* | (2006.01) |
| *H01L 31/02* | (2006.01) |
| *H01L 31/0203* | (2014.01) |
| *H04N 5/225* | (2006.01) |
| *B23K 101/42* | (2006.01) |

(52) U.S. Cl.
CPC ............ *B23K 3/0623* (2013.01); *H01L 21/56* (2013.01); *H01L 25/10* (2013.01); *H01L 31/02002* (2013.01); *H01L 31/0203* (2013.01); *B23K 2101/42* (2018.08); *H01L 23/3121* (2013.01); *H01L 2224/73204* (2013.01); *H04N 5/2253* (2013.01); *H04N 2005/2255* (2013.01)

(58) Field of Classification Search
CPC ............ H04N 2005/2255; H01L 21/56; H01L 23/3121; H01L 24/14636
See application file for complete search history.

(56) References Cited

U.S. PATENT DOCUMENTS

| | | | |
|---|---|---|---|
| 2014/0003018 A1* | 1/2014 | Fujimori | A61B 1/051 361/783 |
| 2014/0264697 A1* | 9/2014 | Nakayama | H04N 5/2253 257/432 |
| 2014/0367156 A1* | 12/2014 | Sekido | H05K 1/183 174/260 |
| 2015/0351218 A1* | 12/2015 | Munakata | H05K 1/0206 361/761 |

FOREIGN PATENT DOCUMENTS

| | | |
|---|---|---|
| JP | 2000307238 A | 11/2000 |
| JP | 2001024312 A | 1/2001 |
| JP | 2006025852 A | 7/2006 |
| JP | 2006216631 A | 8/2006 |
| JP | 2009239223 A | 10/2009 |
| JP | 2011188375 A | 9/2011 |
| JP | 2012-084742 A | 4/2012 |
| WO | WO2011030608 A1 | 3/2011 |

OTHER PUBLICATIONS

International Search Report dated Jun. 2, 2015 issued in PCT/JP2015/058345.

* cited by examiner

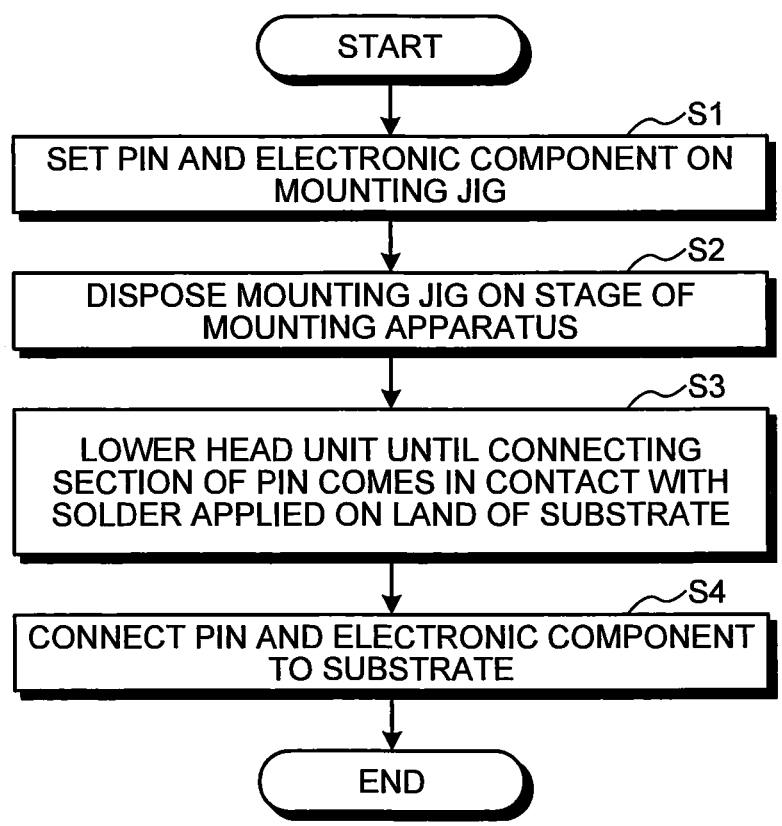

IMAGING APPARATUS INCLUDING AN IMAGE SENSOR CHIP MOUNT ASSEMBLY

CROSS REFERENCES TO RELATED APPLICATIONS

This application is a continuation of PCT international application Ser. No. PCT/JP2015/058345, filed on Mar. 19, 2015 which designates the United States, incorporated herein by reference, and which claims the benefit of priorities from Japanese Patent Application No. 2014-059188, filed on Mar. 20, 2014 and from Japanese Patent Application No. 2015-004487, filed on Jan. 13, 2015, incorporated herein by reference.

BACKGROUND

1. Technical Field

The disclosure relates to a method for manufacturing a mount assembly including a pin and an electronic component that are connected on a same surface of a substrate, a mounting jig, an apparatus for manufacturing the mount assembly, an imaging apparatus, and an endoscope apparatus.

2. Related Art

There is a known endoscope configured to be inserted into a cavity of a subject for observation of a site to be examined. This type of endoscope is widely used in a medical field, or the like. The endoscope incorporates an electronic circuit module formed by mounting electronic components such as an image sensor on a distal end portion of a flexible elongated insertion tool. In view of feasibility in introducing to a patient, there is a demand for enhancing the distal end portion of the insertion tool to be slimmer and smaller.

A method for manufacturing a package has been proposed in which an electronic apparatus has electronic components mounted on a substrate and has a cuboid shape sealed with resin, with a terminal electrode being exposed on a side or top surface of the electronic apparatus (for example, refer to JP 2001-24312 A). The electronic apparatus manufactured by this method includes the terminal electrode on the side or top surface thereof, and connecting positions with a motherboard or other electronic apparatuses can be adjustable, which makes it possible to achieve a small-sized apparatus. Also refer to JP 2000-307238 A.

SUMMARY

In some embodiments, provided is a method for manufacturing a mount assembly in which a plurality of pins and a plurality of electronic components are connected to a same surface of a substrate, each of the plurality of pins including a connecting section and a shaft section having a diameter smaller than that of the connecting section, a height of each of the plurality of electronic components being not larger than that of each of the plurality of pins when being mounted. The method includes: a setting step of setting the plurality of pins and the plurality of electronic components so as to be aligned; and a connection step of disposing the plurality of pins and the plurality of electronic components which are aligned, on a stage of a mounting apparatus, lowering a head unit of the mounting apparatus on which the substrate is adsorbed, and connecting the plurality of pins and the plurality of electronic components collectively to the surface of the substrate by applying heat and pressure while solder applied to a land on the substrate and the connecting section of each of the plurality of pins are in contact with each other.

In some embodiments, provided is a mounting jig for connecting a plurality of pins and a plurality of electronic components to a same surface of a substrate, each of the plurality of pins including a connecting section and a shaft section having a diameter smaller than that of the connecting section, a height of each of the plurality of electronic components being not larger than that of each of the plurality of pins when being mounted. The mounting jig includes: a plurality of pin insertion holes into each of which the shaft section of each of the pins is configure to be inserted; and a plurality of electronic component insertion holes into which the electronic components respectively are configured to be inserted. When the pins and the electronic components are set into the pin insertion holes and the electronic component insertion holes, respectively, a top surface of the connecting section of each of the pins and a top surface of each of the electronic components are located above a top surface of the mounting jig, and the top surface of each of the electronic components is located lower than the top surface of the connecting section of each of the pins.

In some embodiments, provided is an apparatus for manufacturing a mount assembly in which a plurality of pins and a plurality of electronic components are connected to a same surface of a substrate, a height of each of the plurality of electronic components being not larger than that of each of the plurality of pins. The apparatus includes: the mounting jig; a stage on which the mounting jig, onto which the pins and the electronic components are set, is configured to be placed; and a head unit that includes: a holding unit configured to hold the substrate by adsorption; a drive unit configured to vertically move the substrate that is held, such that solder applied to a land on the substrate and a connecting section of each of the pins come in contact with each other; and a heating and pressurizing unit configured to heat the solder applied to the land on the substrate and to apply pressure to the connecting section of each of the pins being in contact with the substrate.

In some embodiments, an imaging apparatus includes an image sensor chip and a mount assembly. The mount assembly includes: a substrate; a plurality of first pins which is mounted on a first surface of the substrate and each of which has a first connecting section and a first shaft section having a diameter smaller than that of the first connecting section; at least one first electronic component which is mounted on the first surface of the substrate and whose height is not larger than that of each of the first pins when being mounted; a first resin sealant configured to seal the first surface so as to expose an end face of the first shaft section opposite to where the first connecting section is provided; a plurality of second pins which is mounted on a second surface of the substrate and each of which has a second connecting section and a second shaft section having a diameter smaller than that of the second connecting section; at least one second electronic component which is mounted on the second surface of the substrate and whose height is not larger than that of each of the second pins when being mounted; and a second resin sealant configured to seal the second surface so as to expose an end face of the second shaft section opposite to where the second connecting section is provided. The image sensor chip includes: a light receiving unit configured to perform photoelectric conversion on an incident optical signal; and a back-surface electrode provided on a surface facing the light receiving unit by through-wiring. The first shaft section exposed on the first resin sealant is connected to the back-surface electrode, and thereby the image sensor chip is connected to the mount assembly.

In some embodiments, an endoscope apparatus includes an insertion unit having the imaging apparatus at a distal end of the insertion unit.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3 is a flowchart illustrating steps of manufacturing a mount assembly according to the first embodiment of the present invention;

DETAILED DESCRIPTION

Hereinafter, reference will be made to a mounting jig and a method for manufacturing a mount assembly as modes for carrying out the invention (hereinafter, referred to as embodiment(s)). The present invention is not intended to be limited by these embodiments. The same reference signs are used to designate the same elements throughout the drawings. The drawings are schematic, and the relationship between the thickness and the width of individual members and the ratio between the members are different from an actual case. There are portions having different dimensions and ratios even between the drawings.

First Embodiment

Figure 1:
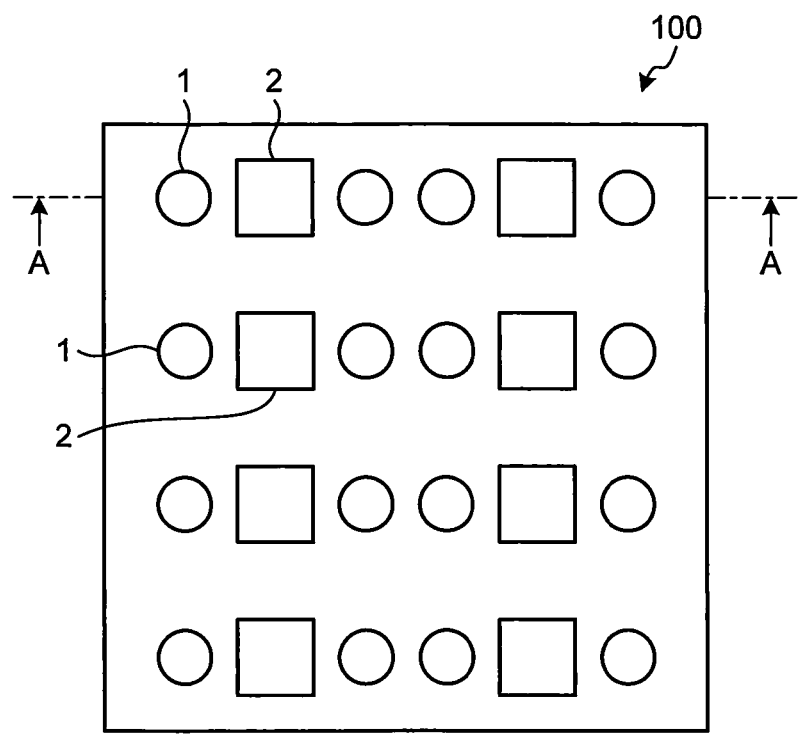
FIG. 1 is a top view schematically illustrating a mounting jig according to a first embodiment of the present invention.
Figure 2:
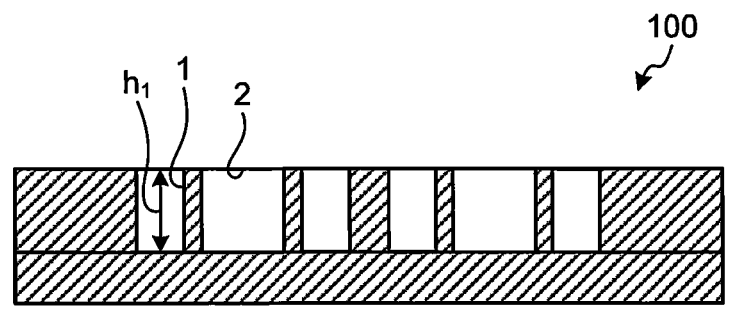
FIG. 2 is a cross-sectional view of the mounting jig illustrated in FIG. 1, taken along line A-A.

FIG. 1 is a top view schematically illustrating a mounting jig according to a first embodiment of the present invention. FIG. 2 is a cross-sectional view of the mounting jig illustrated in FIG. 1, taken along line A-A. As illustrated in FIG. 1, a mounting jig 100 includes a plurality of pin insertion holes 1 into which pins are configured to be inserted and a plurality of electronic component insertion holes 2 into which electronic components are configured to be inserted.

Figure 4A:
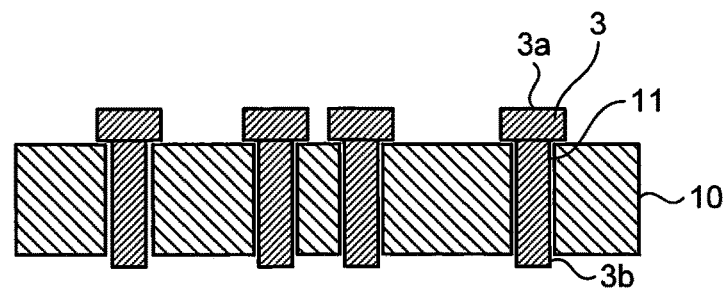
FIG. 4A is a diagram illustrating steps of manufacturing the mount assembly according to the first embodiment of the present invention.

As illustrated in FIG. 4A, or the like, a pin 3 set into the mounting jig 100 includes a disc-shaped connecting section 3a and a shaft section 3b having a diameter smaller than the connecting section 3a. The shaft section 3b is inserted into the pin insertion hole 1. The pin insertion hole 1 has a diameter to which the shaft section 3b is insertable and a depth $h_1$ shorter than the length of the shaft section 3b in an axial direction. The pin insertion hole 1 preferably has the depth $h_1$ that is half or more of a length $h_2$ of the pin 3 (refer to FIG. 4G). The pin 3 functions as a via in the mount assembly described below and is formed of a highly conductive metal material.

The electronic component insertion hole 2 is formed such that a cuboid shape electronic component can be inserted into this hole. On the mounting jig 100, the depth of the electronic component insertion hole 2 is equal to the depth of the pin insertion hole 1, namely, the depth $h_1$. Alternatively, the depth may be adjusted according to the height of the electronic component. The pin insertion hole 1 and the electronic component insertion hole 2 are formed corresponding to the arrangement of the pin 3 and the electronic component of the mount assembly to be manufactured. Even when the depth of the electronic component insertion hole 2 is changed to differ from the depth of the pin insertion hole 1, it is preferable that the top surface of the electronic component is lower than the top surface of the connecting section 3a of the pin 3.

Figure 4B:
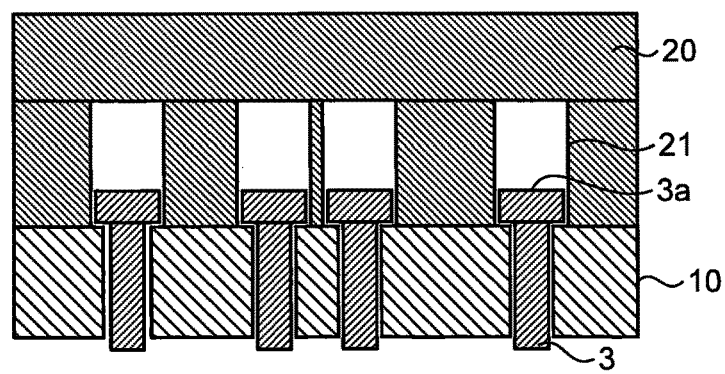
FIG. 4B is a diagram illustrating steps of manufacturing the mount assembly according to the first embodiment of the present invention.
Figure 4C:
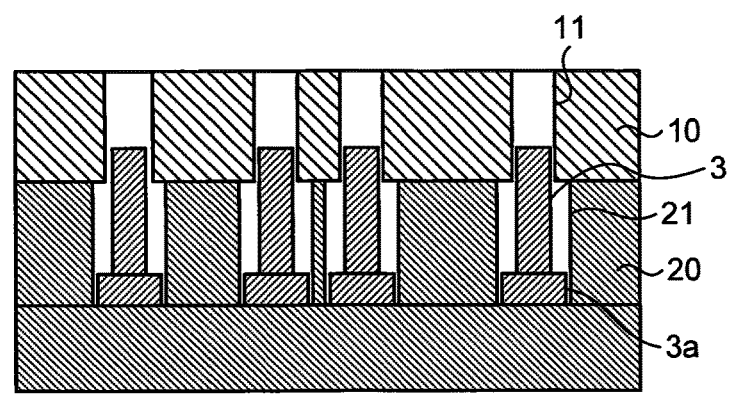
FIG. 4C is a diagram illustrating steps of manufacturing a mount assembly according to the first embodiment of the present invention.
Figure 4D:
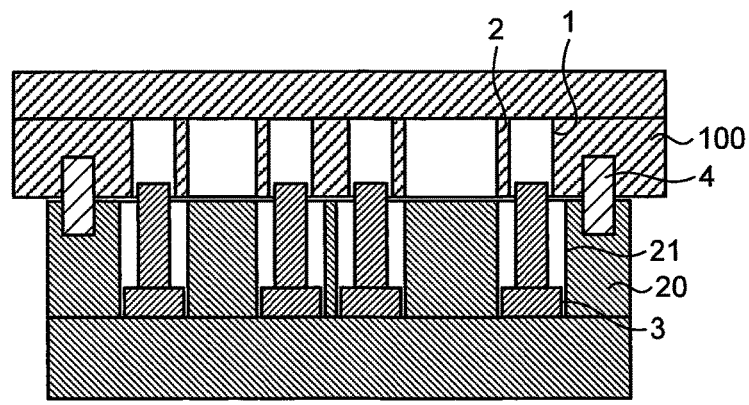
FIG. 4D is a diagram illustrating steps of manufacturing the mount assembly according to the first embodiment of the present invention.
Figure 4E:
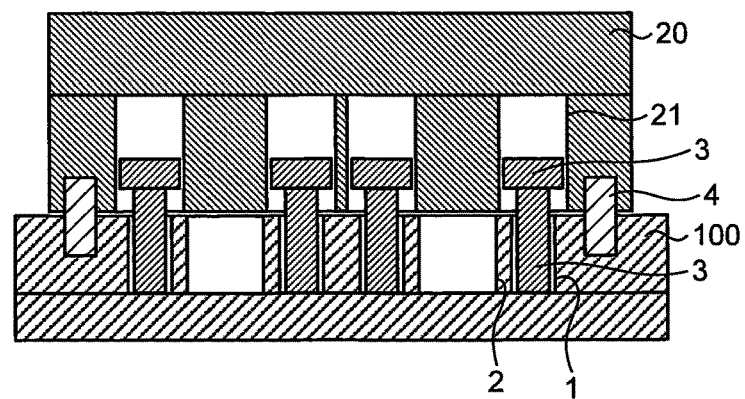
FIG. 4E is a diagram illustrating steps of manufacturing the mount assembly according to the first embodiment of the present invention.

Next, a method of manufacturing a mount assembly using the mounting jig 100 will be described. FIG. 3 is a flowchart illustrating steps of manufacturing the mount assembly according to the first embodiment of the present invention. FIGS. 4A to 4Q are diagrams illustrating steps of manufacturing the mount assembly according to the first embodiment of the present invention. In FIGS. 4I to 4J, a holding unit 56, a drive unit 57, a heating and pressurizing unit 58, and a control unit 59, illustrated in FIG. 4H, are omitted.

First, reference will be made to a setting step (step S1) of setting the pin 3 and an electronic component onto the mounting jig 100. The pin 3 having a small diameter is first set into an insertion jig 10 illustrated in FIG. 4A before being inserted into the mounting jig 100. A through-hole 11 whose diameter is substantially equal to that of the shaft section 3b is formed in the insertion jig 10. With the pin 3 being placed on the insertion jig 10, the insertion jig 10 is shaken while performing suction from below the insertion jig 10 using a vacuum pump, or the like. As a result, the shaft section 3b is inserted into the through-hole 11, and the pin 3 is set into the insertion jig 10.

After the pin 3 has been set into the insertion jig 10, the pin 3 is transferred from the insertion jig 10 to a transfer jig 20. As illustrated in FIGS. 4B and 4C, the transfer jig 20 includes an insertion hole 21 having a diameter substantially equal to the diameter of the connecting section 3a. As illustrated in FIG. 4B, the transfer jig 20 is put on the insertion jig 10 from the side where the connecting section 3a in the insertion jig 10 protrudes. Thereafter, as illustrated in FIG. 4C, the insertion jig 10 and the transfer jig 20 are reversed so as to avoid displacement of these jigs, and thus, the pin 3 is transferred from the insertion jig 10 to the transfer jig 20.

After the pin 3 has been transferred to the transfer jig 20, the pin 3 is transferred from the transfer jig 20 to the mounting jig 100. As illustrated in FIG. 4D, the mounting jig 100 is put on the transfer jig 20 from the side where the insertion hole 21 into which the pin 3 is inserted is provided. The mounting jig 100 and the transfer jig 20 are positioned by a positioning pin 4. Thereafter, as illustrated in FIG. 4E, the transfer jig 20 and the mounting jig 100 are reversed, and thus, the pin 3 is transferred from the transfer jig 20 into the pin insertion hole 1 of the mounting jig 100.

Figure 4F:
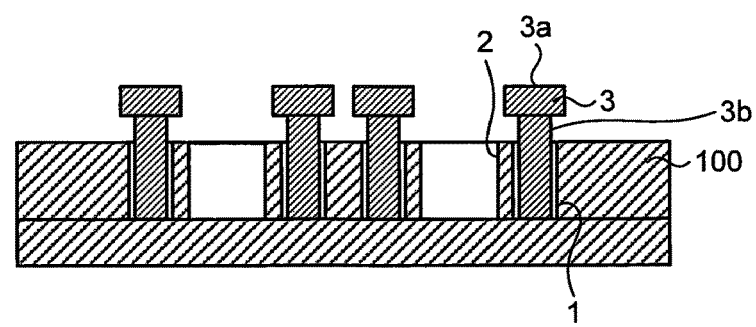
FIG. 4F is a diagram illustrating steps of manufacturing a mount assembly according to the first embodiment of the present invention.
Figure 4G:
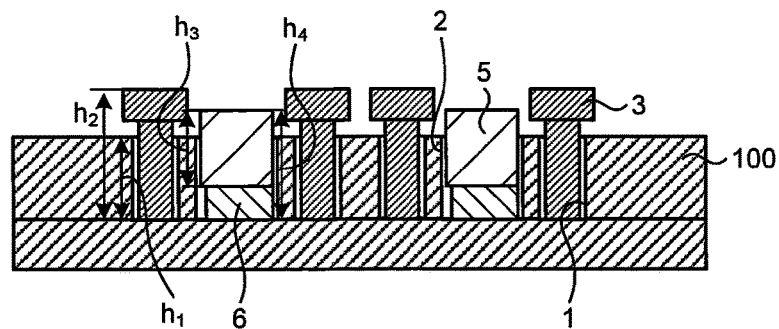
FIG. 4G is a diagram illustrating steps of manufacturing a mount assembly according to the first embodiment of the present invention.
Figure 4H:
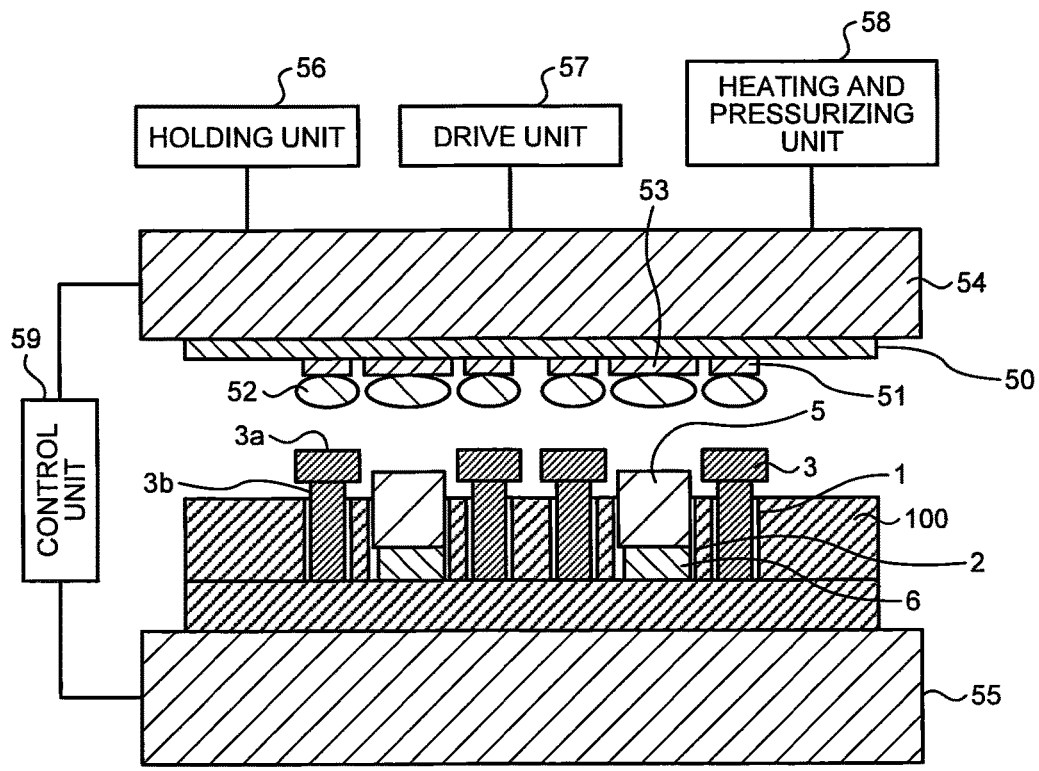
FIG. 4H is a diagram illustrating steps of manufacturing a mount assembly according to the first embodiment of the present invention.
Figure 4I:
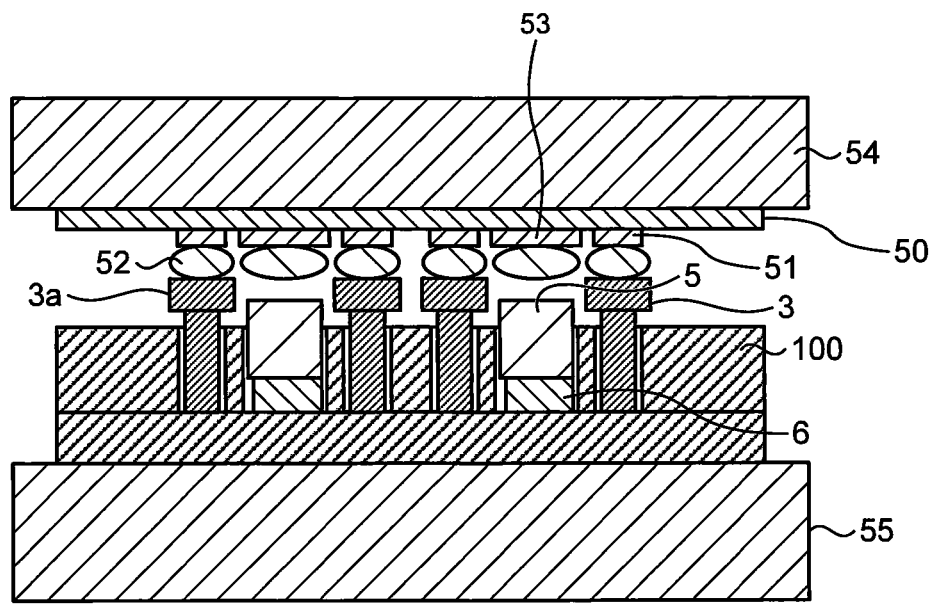
FIG. 4I is a diagram illustrating steps of manufacturing a mount assembly according to the first embodiment of the present invention.
Figure 4J:
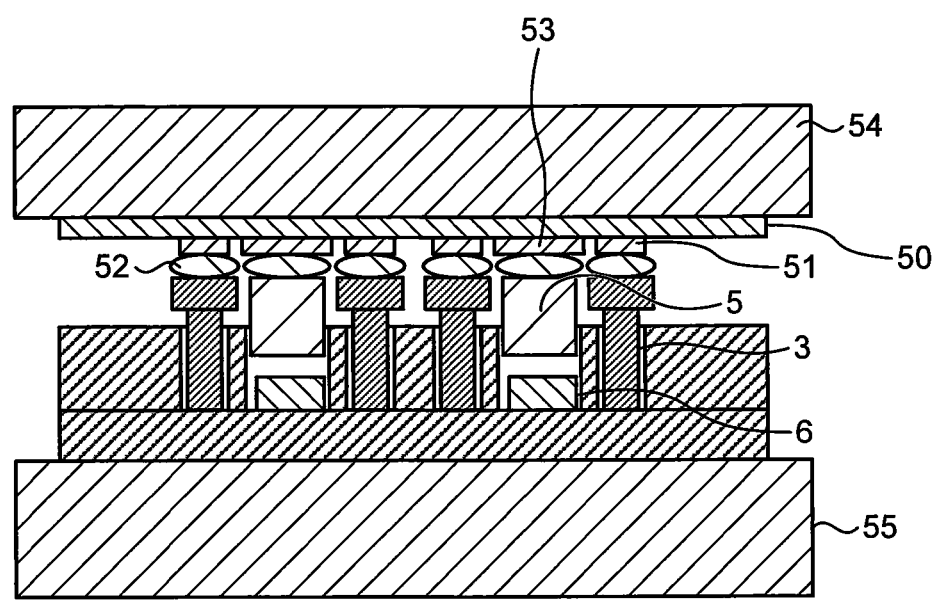
FIG. 4J is a diagram illustrating steps of manufacturing a mount assembly according to the first embodiment of the present invention.

As a result of the transfer of the pin 3 by the transfer jig 20, as illustrated in FIG. 4F, the pin 3 is inserted into each of the pin insertion holes 1 of the mounting jig 100, and as illustrated in FIG. 4G, an electronic component 5 such as a capacitor is manually inserted into each of the electronic component insertion holes 2, which are unoccupied. It is possible to insert the electronic component 5 alone into the electronic component insertion hole 2. However, in a case where a height $h_3$ of the electronic component 5 is smaller than the depth $h_1$ of the electronic component insertion hole 2, as illustrated in FIG. 4G, a spacer 6 is preferably inserted below the electronic component 5 to arrange the top surface of the electronic component 5 to be positioned above the mounting jig 100, and the top surface of the pin 3 and the top surface of the electronic component 5 are preferably adjusted with each other. The height $h_3$ of the electronic component 5 mounted on the substrate simultaneously with the pin 3 is typically not larger than the height $h_2$ of the pin 3. In a case where the height $h_3$ of the electronic component 5 is smaller than the depth $h_1$ of the electronic component insertion hole 2, it would be preferable to use the spacer 6 such that the height $h_4$ of the top surface of the electronic component 5 is larger than the depth $h_1$ of the electronic component insertion hole 2 and not larger than the height $h_2$ of the pin 3. Alternatively, the height of the upper surface of the electronic component 5 can be adjusted without using the spacer 6 by forming the mounting jig 100 such that the depth of the electronic component insertion hole 2 is smaller than the depth of the pin insertion hole 1.

In a case where the mounting surface of the electronic component 5 is defined, it would be necessary to manually insert the electronic component 5 into the electronic component insertion hole 2. However, in a case where the mounting surface of the electronic component 5 has no restriction, it would be allowable, similarly to the case of the pin 3, to insert the electronic component 5 into the electronic component insertion hole 2 using an insertion jig and a transfer jig. The mounting methods described above and illustrated in FIGS. 4A to 4G correspond to step S1 in FIG. 3.

After the pin 3 and the electronic component 5 have been set into the mounting jig 100 (step S1), the mounting jig 100 on which the pin 3 and the electronic component 5 are set is arranged on a stage of the mounting apparatus (step S2). The pin 3 and the electronic component 5 are connected to the substrate using the mounting apparatus. As illustrated in FIG. 4H, the mounting apparatus includes a stage 55, a holding unit 56, a drive unit 57, a head unit 54, and a control unit 59. The pin 3 and the electronic component 5 are set into the mounting jig 100, and the mounting jig 100 is placed on the stage 55. The holding unit 56 holds a substrate 50 by adsorption. The drive unit 57 is configured to vertically move the substrate 50 being held such that solder 52 applied beforehand to a land 51 on the substrate 50 and the connecting section 3a of the pin 3 come in contact with each other. The head unit 54 includes a heating and pressurizing unit 58 configured to heat the solder 52 applied beforehand to the land 51 on the substrate 50 and apply pressure to the connecting section 3a of the pin 3 that comes in contact with the substrate 50. The control unit 59 controls each unit.

First, as illustrated in FIG. 4H, the mounting jig 100 is placed on the stage 55 of the mounting apparatus. On the substrate 50, the solder 52 has been applied to the land 51 for connecting the pin 3 and to a land 53 for connecting the electronic component 5. The substrate 50 is held by the holding unit 56 and then set onto the head unit 54 side. The mounting method in FIG. 4H corresponds to step S2 in FIG. 3.

The mounting jig 100 is set onto the stage 55 of the mounting apparatus (step S2), and thereafter, the head unit 54 of the mounting apparatus on which the substrate 50 is adsorbed, is lowered to cause the solder 52 applied to the land 51 of the substrate 50 and the connecting section 3a of the pin 3 to come in contact with each other (step S3). As illustrated in FIG. 4I, the head unit 54 holding the substrate 50 is lowered by the drive unit 57 until the solder 52 and the connecting section 3a of the pin 3 come in contact with each other. In a state where the solder 52 is in contact with the connecting section 3a of the pin 3, pressure and heat are simultaneously applied by the heating and pressurizing unit 58, thereby melting the solder 52. In a state before heat and pressure are applied, as illustrated in FIG. 4I, in a case where the top surface of the electronic component 5 is adjusted to be lower than the top surface of the pin 3, the solder 52 on the land 53 and the electronic component 5 are not in contact with each other even when the head unit 54 is lowered. This mounting method illustrated in FIG. 4I corresponds to step S3 in FIG. 3. However, as illustrated in FIG. 4J, after the heat and pressure have melted the solder 52 on the land 53, lowering the head unit 54 by a difference between the height $h_2$ of the pin 3 and the height $h_4$ of the top surface of the electronic component 5 would allow the melted solder 52 to come in contact with the top surface of the electronic component 5. As a result, the electronic component 5 is sucked up to be mounted on the substrate 50 together with the pin 3. In this manner, in a case where the top surface of the electronic component 5 is adjusted to be lower than the top surface of the pin 3, it is possible to reliably mount the electronic component 5 onto the substrate 50 without applying unnecessary pressure.

Figure 4K:
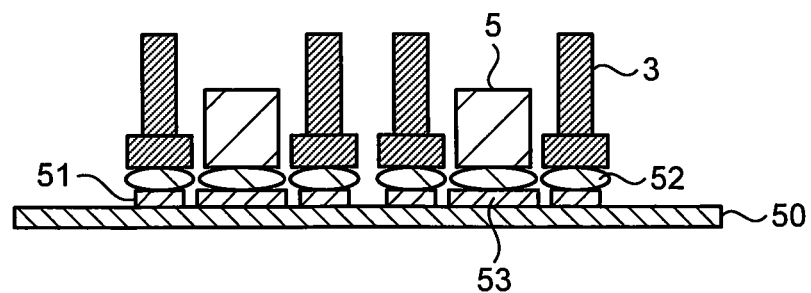
FIG. 4K is a diagram illustrating steps of manufacturing the mount assembly according to the first embodiment of the present invention.

The pin 3 and the electronic component 5 are collectively connected to the substrate 50 by heating and pressurization (step S4), and thereafter, the substrate 50 and the mounting jig 100 are removed from the mounting apparatus. Remaining flux is cleansed and the substrate 50 is separated from the mounting jig 100, as illustrated in FIG. 4K. The mounting methods illustrated in FIGS. 4J to 4K correspond to step S4 in FIG. 3. Even in a case where the depth of the electronic component insertion hole 2 of the mounting jig 100 is equal to the depth of the pin insertion hole 1 of the mounting jig 100, the distance between the top surface of the connecting section 3a of the pin 3 and the land 51 surface on the substrate 50 is shorter than the distance between the top surface of the electronic component 5 and the land 53 surface on the substrate 50 if the land 51 connected to the pin 3 has a thickness greater than the thickness of the land 53 connected to the electronic component 5. Moreover, by providing the lands 51 and 53 on the substrate 50 with a conductive protrusion (such as Au stud bump and conductive paste) that deforms by load at the time of mounting, it is possible to reduce the load applied to the substrate 50 at the time of mounting.

Figure 4L:
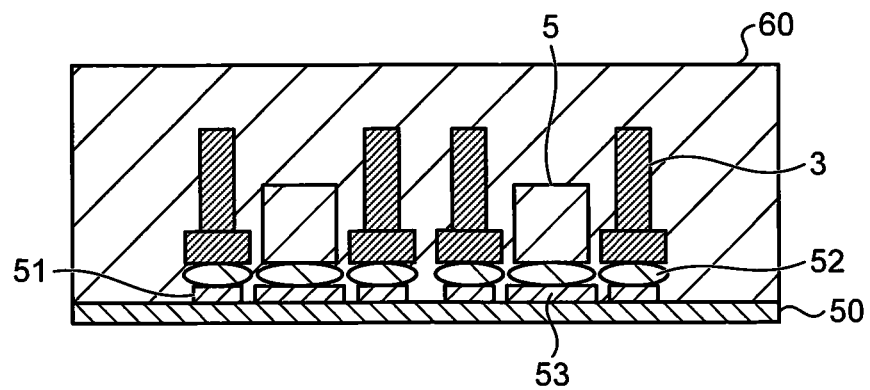
FIG. 4L is a diagram illustrating steps of manufacturing a mount assembly according to the first embodiment of the present invention.
Figure 4M:
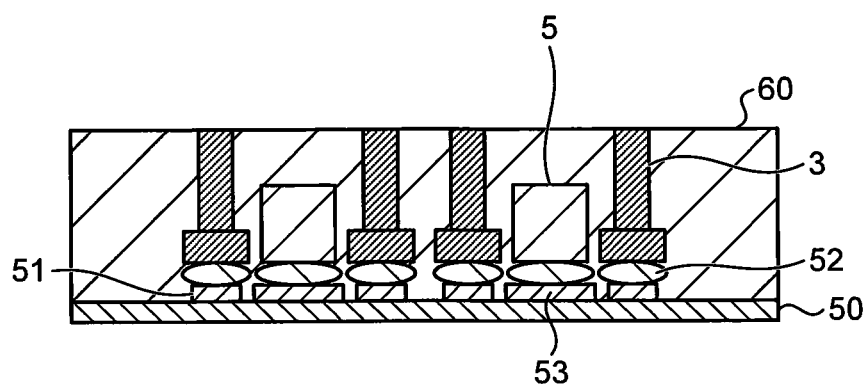
FIG. 4M is a diagram illustrating steps of manufacturing the mount assembly according to the first embodiment of the present invention.

As illustrated in FIG. 4L, the surface of the substrate 50, on which the pin 3 and the electronic component 5 are mounted, is sealed with a resin sealant 60 and ground so as to expose an end face of the pin 3 on the resin sealant 60 surface (FIG. 4M).

Figure 4N:
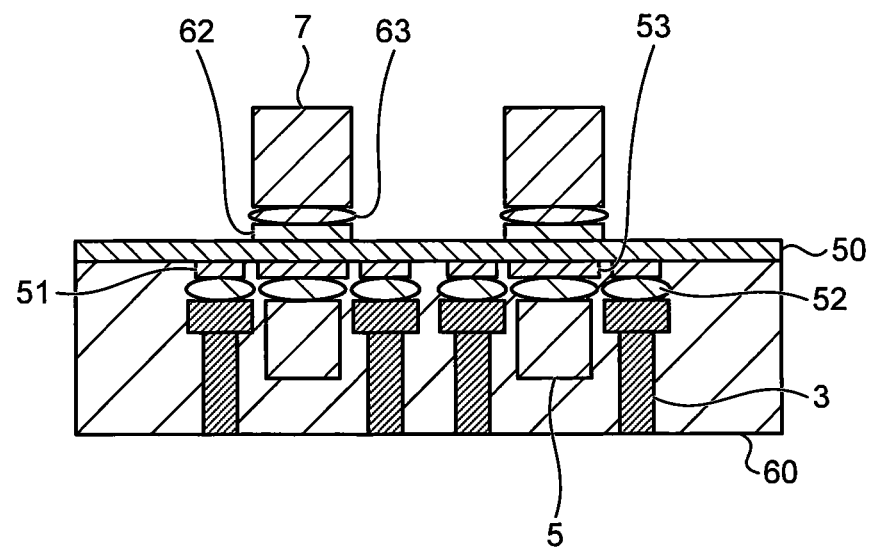
FIG. 4N is a diagram illustrating steps of manufacturing the mount assembly according to the first embodiment of the present invention.
Figure 4O:
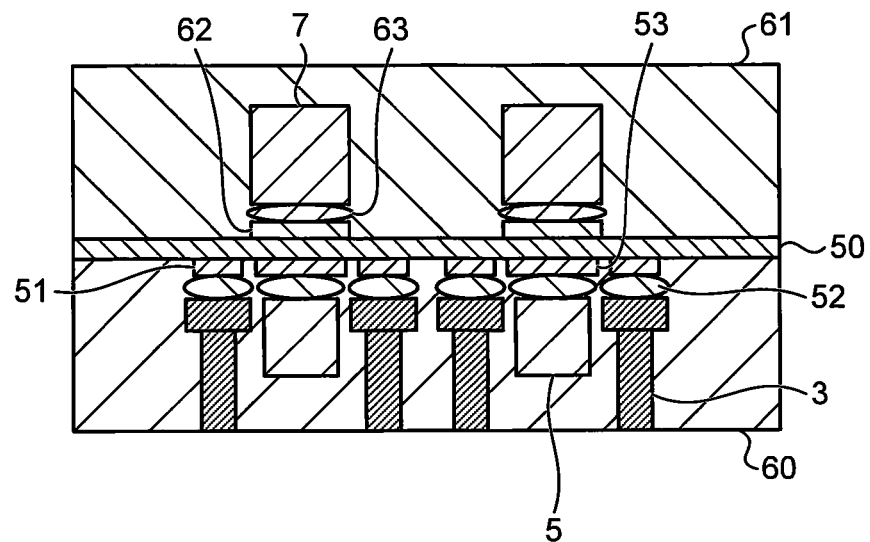
FIG. 4O is a diagram illustrating steps of manufacturing the mount assembly according to the first embodiment of the present invention.

On a back surface of the substrate 50 opposite to where the pin 3 is mounted, another electronic component 7 is connected to a land 62 via solder 63 (FIG. 4N), and the mounting surface of the electronic component 7 is also sealed with resin sealant 61 (FIG. 4O).

Figure 4P:
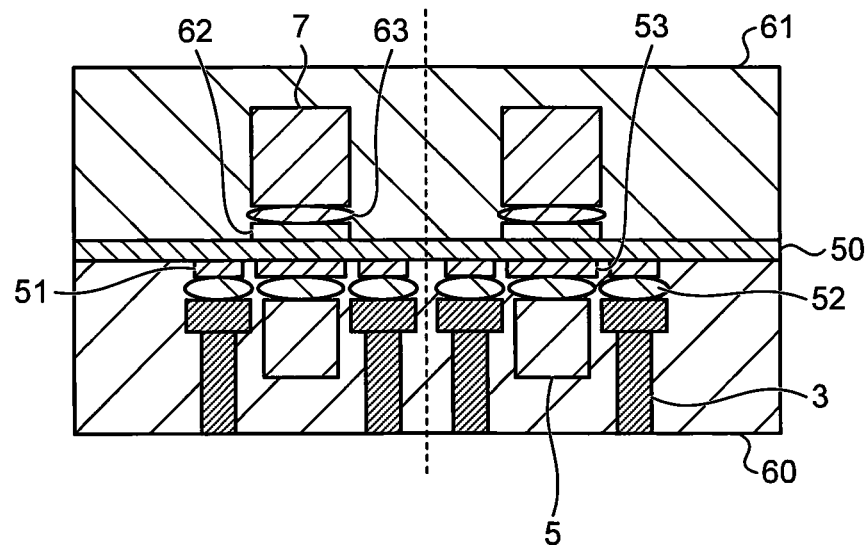
FIG. 4P is a diagram illustrating steps of manufacturing the mount assembly according to the first embodiment of the present invention.
Figure 4Q:
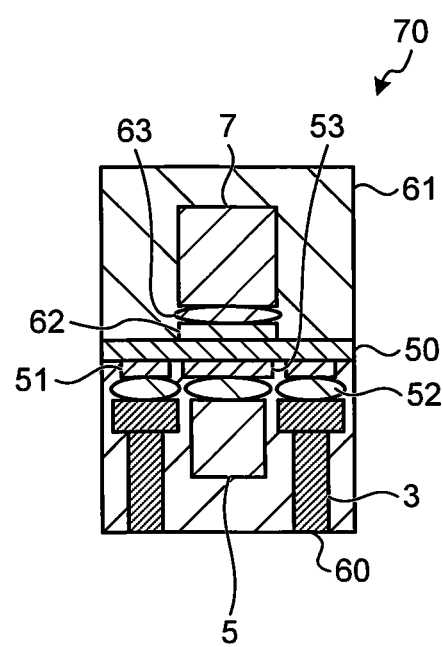
FIG. 4Q is a diagram illustrating steps of manufacturing the mount assembly according to the first embodiment of the present invention.

With components mounted on both sides of the substrate 50, the substrate 50 is divided along a specified cutting line indicated by the dotted line illustrated in FIG. 4P to provide a single mount assembly 70 (FIG. 4Q).

According to the present embodiment, it is possible to collectively connect the pin and the electronic component to the substrate and to easily manufacture the mount assembly. Moreover, when the pin and the electronic component are set into the mounting jig, the positions of the upper surfaces of the pin and the electronic component are adjusted. This makes it possible to achieve connection without applying unnecessary pressure toward the electronic components, leading to reduction of stress on the electronic components.

Figure 5:
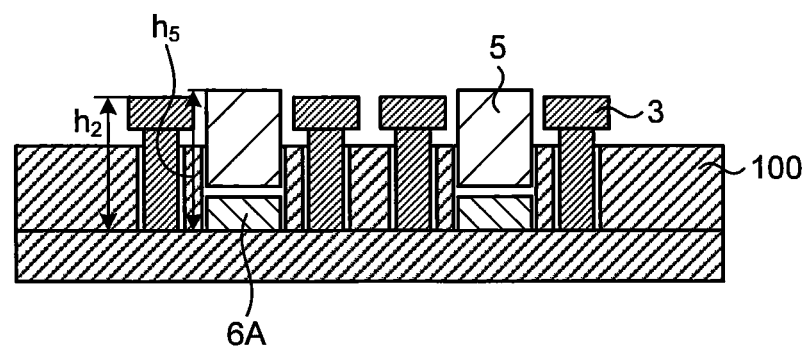
FIG. 5 is a cross-sectional view schematically illustrating a mounting jig according to a modification of the first embodiment of the present invention.

It is also possible to use a spacer formed of an elastic body as a spacer for the mounting jig 100. In a case where a spacer 6A formed of an elastic body is used, it is preferable, as illustrated in FIG. 5, to arrange the height $h_5$ of the top surface of the electronic component 5 to be higher than the height $h_2$ of the top surface of the pin 3. In a case where the top surface of the electronic component 5 is higher than the top surface of the pin 3, the solder 52 comes in contact with the electronic component 5 first. However, since the spacer 6A formed of an elastic body is used, pressure is mainly applied to the pin 3. With this arrangement, it is possible to easily mount the pin 3 in an upstanding state, and to reliably perform connection with the electronic component 5 while reducing stress on the electronic component 5.

A method using the mounting jig 100 is described as a mounting method to set the pin 3 and the electronic component 5 to be aligned. The method is not intended to be limited to this but other methods may be used for arranging them in line. For example, it is allowable to arrange the pin 3 and the electronic component 5 in line and fix them using a temporarily-adhesive sheet or a member on which a temporary adhesive is patterned. Alternatively, it is also allowable to place a magnet on a stage abutting the back surface of the substrate 50 corresponding to the arrangement positions of the pin 3 and the electronic component 5 and to use a method to fix the pin and the electronic component using a magnetic force.

Second Embodiment

Figure 6:
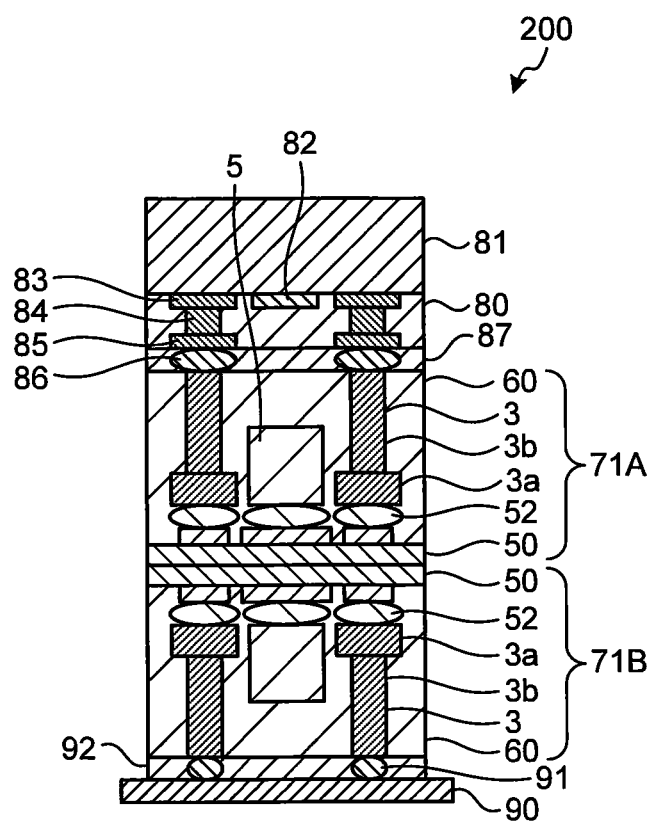
FIG. 6 is a cross-sectional view of an imaging apparatus according to a second embodiment of the present invention.

An imaging apparatus according to a second embodiment includes a mount assembly manufactured by the method of the first embodiment, and an image sensor chip. FIG. 6 is a cross-sectional view of the imaging apparatus according to the second embodiment.

As illustrated in FIG. 6, an imaging apparatus 200 includes an image sensor chip 80, two mount assemblies 71A and 71B, and a motherboard 90.

The image sensor chip 80 is formed of a CMOS device, or the like, and includes a light receiving unit 82, a peripheral circuit unit 83, and a back-surface electrode 85. The light receiving unit 82 performs photoelectric conversion on an incident optical signal. The peripheral circuit unit 83 is formed in the vicinity of the light receiving unit 82. The back-surface electrode 85 is formed on a surface facing the light receiving unit 82 by through-wiring 84 formed of through-silicon via (TSV), or the like. A glass lid 81 is pasted on a front surface side. The glass lid 81 is configured to protect the light receiving unit 82 via a joint layer. A wiring layer (not illustrated) is formed on a back surface of the image sensor chip 80. The wiring layer has a multi-layer wiring structure. It is preferable that the image sensor chip 80 is a chip size package (CSP) formed by performing wiring, electrode formation, resin seal, and dicing, on an image sensor in a wafer state, and that finally the size of the image sensor becomes the size of the image sensor chip.

The mount assemblies 71A and 71B share the same structure. Each assembly includes the substrate 50, two pins 3, the electronic component 5, and the resin sealant 60. The pin 3 includes the connecting section 3a and the shaft section 3b whose diameter is smaller than that of the connecting section 3a. The height of the electronic component 5 is not larger than that of the pin 3 when being mounted. The resin sealant 60 seals the mounting surface of the substrate 50 so as to expose an end face of the shaft section 3b opposite to where the connecting section 3a is provided.

The mount assemblies 71A and 71B are formed by the method described in the first embodiment. As illustrated in FIGS. 4A to 4M, the pin 3 and the electronic component 5 mounted on the substrate 50 are sealed with the resin sealant, then, grinding is performed so as to expose the end face of the shaft section 3b of the pin 3 on the resin sealant 60 surface. Then, with no electronic components mounted on the opposite side of the mounting surface of the substrate 50 (steps shown in FIGS. 4N and 4O are omitted), the assembly is divided along a specified cutting line indicated by the dotted line illustrated in FIG. 4P to provide the mount assemblies 71A and 71B.

On each of the two mount assemblies 71A and 71B, the mounting surface and the opposite surface (with no electronic component 5, or the like, being mounted) are mechanically and electrically connected with each other. On the substrate 50, a via (not illustrated) is provided to permit connection, thereby allowing the two mount assemblies 71A and 71B to communicate with each other.

Figure 7:
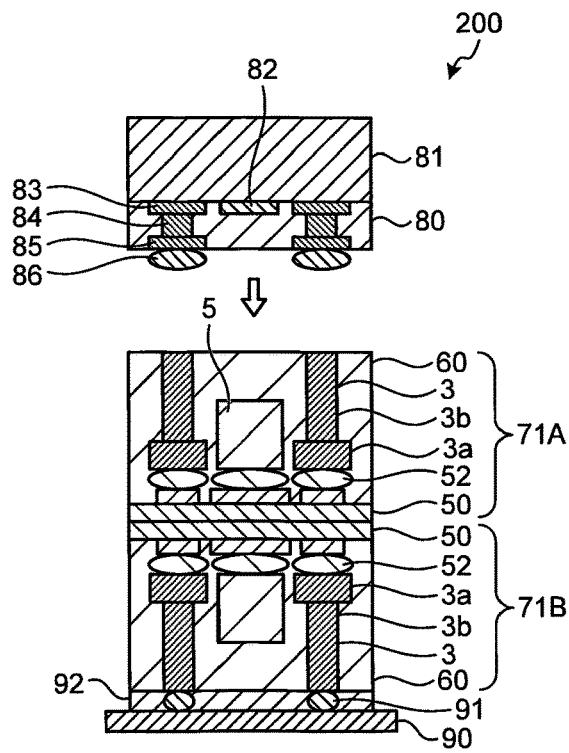
FIG. 7 is a diagram illustrating steps of manufacturing the imaging apparatus in FIG. 6.

The motherboard 90 includes a connection electrode 91 and is connected with an end face of the shaft section 3b exposed on the resin sealant 60 surface of the mount assembly 71B, and surrounding portions are sealed with resin sealant 92. A bump 86 formed of solder is formed on a back-surface electrode 85 of the image sensor chip 80. As illustrated in FIG. 7, the back-surface electrode 85 is connected with the end face of the shaft section 3b exposed on the resin sealant 60 surface of the mount assembly 71A, via the bump 86. Portions around the connecting section are sealed with resin sealant 87.

The imaging apparatus 200 according to the second embodiment uses the mount assemblies 71A and 71B that share the same structure. Alternatively, however, it is allowable to use a mount assembly incorporating different types of pins and electronic components as long as the end faces of the shaft sections of the plurality of pins can be used for connection with the image sensor chip 80 and the motherboard 90. The number of pins 3 incorporated in the mount assemblies 71A and 71B is not limited as long as it is two or more. A similar manner can be applied to the case of the number of incorporated electronic components 5.

Figure 8:
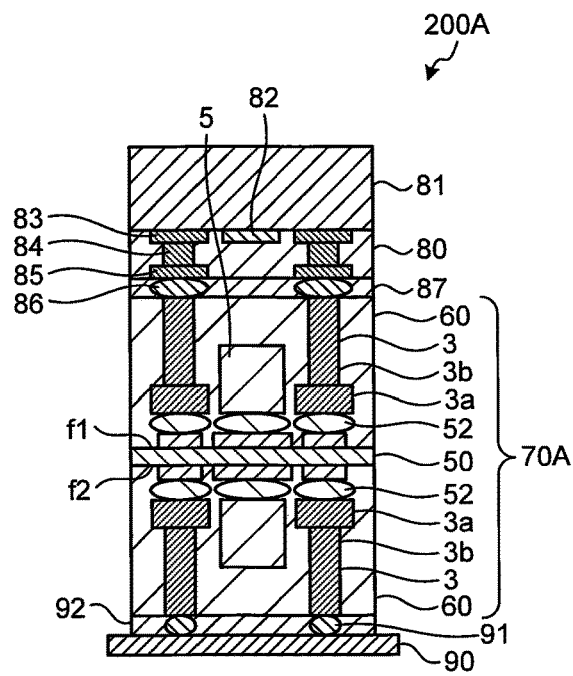
FIG. 8 is a cross-sectional view of an imaging apparatus according to a first modification of the second embodiment of the present invention.

Furthermore, it is also allowable that the pins and electronic components are mounted on both sides of one substrate of the mount assembly. FIG. 8 is a schematic cross-sectional view of an imaging apparatus according to a first modification of the second embodiment.

An imaging apparatus 200A includes the image sensor chip 80, a mount assembly 70A, and the motherboard 90.

On the mount assembly 70A, two pins 3 and one electronic component 5 are mounted on a first surface f1 of the substrate 50, and two pins 3 and one electronic component 5 are also mounted on a second surface f2, namely, the opposite side of the first surface f1, on the substrate 50.

Figure 9:
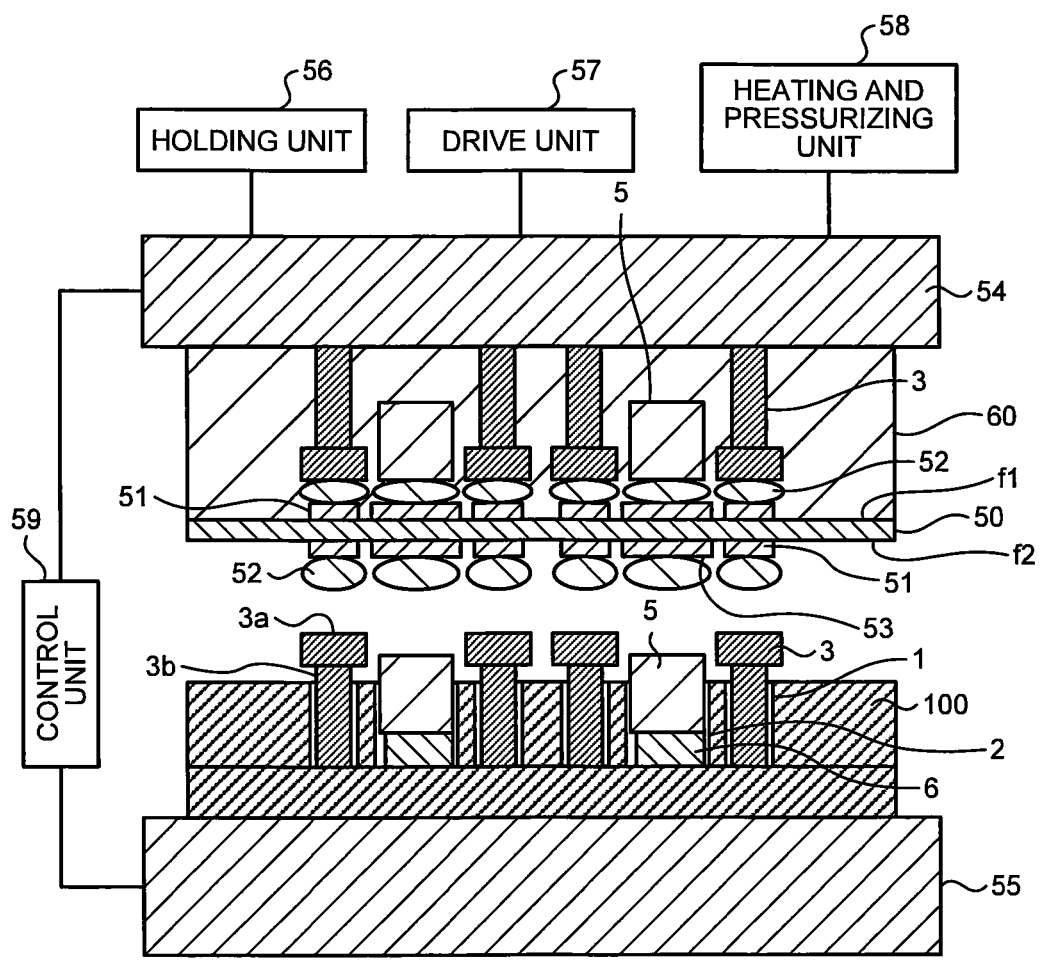
FIG. 9 is a diagram illustrating steps of manufacturing the imaging apparatus in FIG. 8.

The mount assembly 70A is formed by a method described in the first embodiment. Thereafter, as illustrated in FIGS. 4A to 4M, the pin 3 and the electronic component 5 mounted on the first surface f1 of the substrate 50 are sealed with the resin sealant 60, then, grinding is performed so as to expose the end face of the shaft section 3b of the pin 3 on the resin sealant 60 surface. Then, as illustrated in FIG. 9, the pin 3 and the electronic component 5 are mounted on the second surface f2, namely, opposite side of the first surface f1, on the substrate 50. On the substrate 50, a via (not illustrated) is provided to permit communication between the first surface f1 and the second surface f2.

As illustrated in FIG. 9, the pin 3 and the electronic component 5 are set into the mounting jig 100, and the mounting jig 100 is placed on the stage 55 of the mounting apparatus. On the head unit 54, the mount assembly before the cutting, as illustrated in FIG. 4M, is held by the holding unit 56 by adsorption. On the second surface f2 of the mount assembly before the cutting, the solder 52 is applied on a land 51 for connecting the pin 3 and on the land 53 for connecting the electronic component 5. The head unit 54 is lowered by the drive unit 57, and the pin 3 and the land 51 are connected with each other, while the electronic component 5 and the land 53 are connected with each other. The connection is performed similarly to the connection in FIGS. 4H to 4J in the first embodiment. Then, similarly to FIGS. 4L and 4M, the second surface f2 is sealed with the resin sealant 60 and then, grinding is performed so as to expose the end face of the shaft section 3b of the pin 3 on the resin sealant 60 surface. Thereafter, the assembly is divided along a specified cutting line to produce the mount assembly 70A.

On the imaging apparatus 200A according to the first modification of the second embodiment, the pins 3 and electronic components 5 mounted on the first surface f1 are same as those mounted on the second surface f2. Alternatively, however, it is allowable to incorporate different types of pins and electronic components on the first surface f1 and the second surface f2 as long as the end faces of the shaft sections of the plurality of pins can be used for connection with the image sensor chip 80 and the motherboard 90. The number of pins 3 mounted on the first surface f1 and the second surface f2, of the mount assembly 70A, is not limited as long as it is two or more. A similar manner can be applied to the case of the number of electronic components 5 to be mounted.

Figure 10:
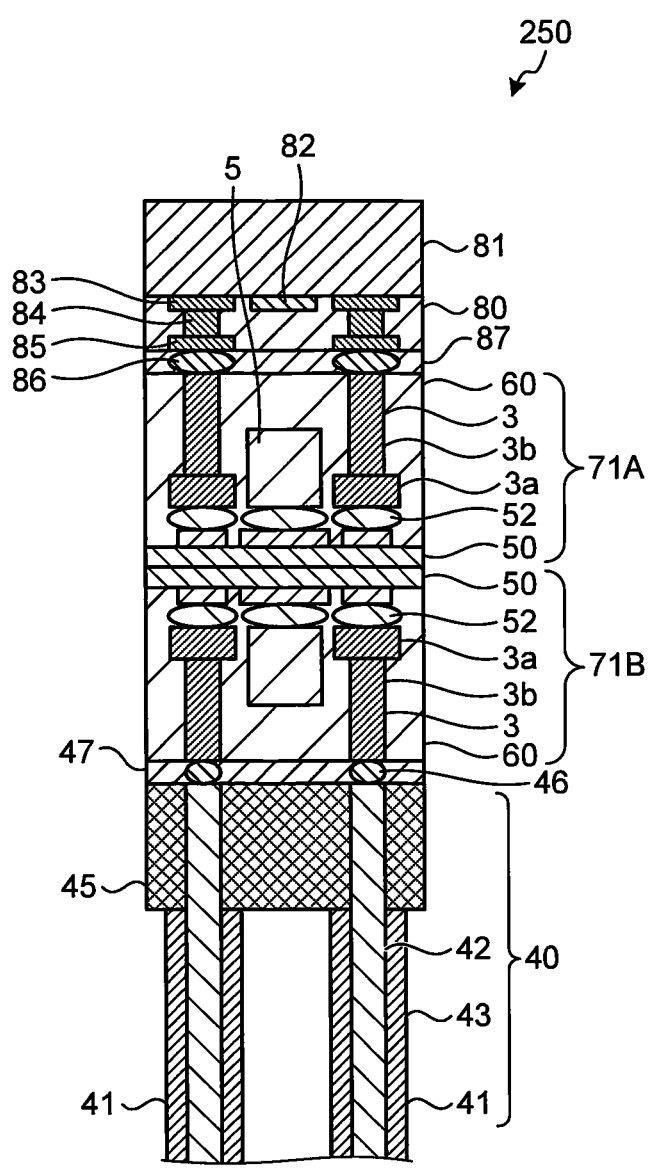
FIG. 10 is a cross-sectional view of an imaging apparatus according to a second modification of the second embodiment of the present invention.

The imaging apparatus may be configured to include a mount assembly manufactured by the method in the first embodiment, an image sensor chip, and a cable assembly. FIG. 10 is a schematic cross-sectional view of the imaging apparatus according to a second modification of the second embodiment.

As illustrated in FIG. 10, an imaging apparatus 250 includes the image sensor chip 80, the two mount assemblies 71A and 71B, and a cable assembly 40.

The cable assembly 40 is produced by scraping outer casing 43 from an end portion of a plurality of cables 41 to expose a cable core 42, and fixing the exposed cable core 42 with a fixing member 45 formed of an insulating material such as resin. The cable core 42 is fixed at a predetermined interval by the fixing member 45, and a connection end face on which the cable core 42 is exposed has undergone grinding processing.

The cable core 42 exposed on the connection end face is connected to the shaft section 3b by a bump 46 formed of solder, or the like, on the shaft section 3b that is exposed on the resin sealant 60 surface of the mount assembly 71B. Portions around the connecting section that connects the cable core 42 with the shaft section 3b are sealed with resin sealant 47.

The mount assembly that connects the cable assembly 40 may be the mount assembly 70A in the first modification.

Figure 11:
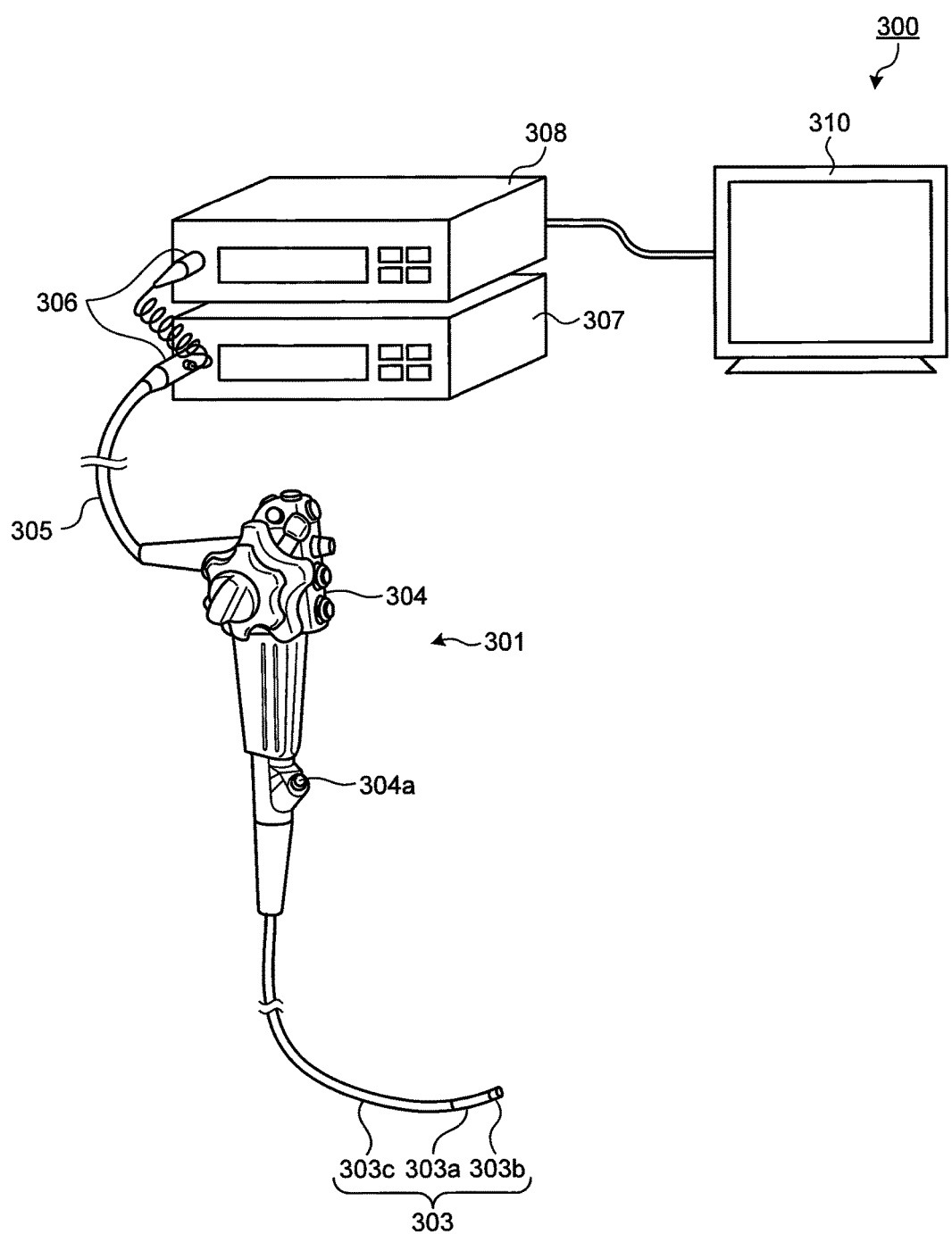
FIG. 11 is a diagram schematically illustrating an overall configuration of an endoscope system using an imaging apparatus.

The above-described imaging apparatus 250 according to the second modification of the second embodiment can be preferably applied to an endoscope apparatus. FIG. 11 is a diagram schematically illustrating an overall configuration of an endoscope system including an imaging apparatus. As illustrated in FIG. 11, an endoscope system 300 includes an endoscope 301, a universal cord 305, a connector 306, a light source apparatus 307, a processor (control apparatus) 308, and a display device 310.

The endoscope 301 captures an in-vivo image of a subject by inserting an insertion unit 303 into the body cavity of the subject and outputs an imaging signal. The imaging apparatus 250 illustrated in FIG. 10 is arranged at a distal end portion 303b and connected to the light source apparatus 307 and the processor 308 via the cable 41 inside the universal cord 305.

The connector 306 is provided at a proximal end of the universal cord 305, connected with the light source apparatus 307 and the processor 308, performs predetermined signal processing on an imaging signal (output signal) output from the imaging apparatus 250 on the distal end portion 303b connected with the universal cord 305, and performs analog-digital (A/D) conversion on the imaging signal and outputs this signal as an image signal.

The light source apparatus 307 includes a while LED, for example. Pulsed while light emitted from the light source apparatus 307 is used as illumination light that is transmitted through the connector 306 and the universal cord 305, and emitted toward the subject from the distal end of the insertion unit 303 of the endoscope 301.

The processor 308 performs predetermined image processing on the image signal output from the connector 306, while controlling the whole endoscope system 300. The display device 310 displays the image signal processed by the processor 308.

An operating unit 304 is provided on the proximal end side of the insertion unit 303 of the endoscope 301. The operating unit 304 includes various buttons and knobs for operating endoscopic functions. The operating unit 304 includes a treatment tool insertion port 304a through which a treatment tool, such as biopsy forceps, an electric knife, and a test probe, is configured to be inserted into the body cavity of the subject.

The insertion unit 303 includes a distal end portion 303b, a bending portion 303a, and a flexible tube portion 303c. The distal end portion 303b is provided with the imaging apparatus 250. The bending portion 303a, bendable in the up-down direction, is continuously arranged at the proximal end side of the distal end portion 303b. The flexible tube portion 303c is continuously arranged at the proximal end side of the bending portion 303a. The bending portion 303a bends in the up-down direction by operating a bending operation knob provided at the operating unit 304. The bending portion 303a is bendable in two directions, namely, up and down directions, for example, in accordance with pulling/loosening of the bending wire inserted into the insertion unit 303.

The endoscope 301 includes a light guide for transmitting illumination light from the light source apparatus 307, and an illumination window is provided at an emission end of the illumination light by the light guide. The illumination window is provided at the distal end portion 303b of the insertion unit 303 and the illumination light is emitted through this window toward the subject.

With the endoscope system 300 configured as above, it is possible to perform observation and diagnosis of a diagnosis target by providing the imaging apparatus 250 at the distal end of the insertion unit 303, and by displaying an image of an organ, or the like, obtained by insertion of the insertion unit 303 into the body of the subject, on the display section of the display device 310.

According to a method for manufacturing a mount assembly, a mounting jig, an apparatus for manufacturing the mount assembly, an imaging apparatus, and an endoscope apparatus of some embodiments, it is possible to connect a plurality of pins and a plurality of electronic components collectively on a same surface of a substrate, and thus, to produce the mount assembly efficiently.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging apparatus comprising:
   an image sensor chip; and
   a mount assembly, wherein
   the mount assembly includes:
      a substrate;
      a plurality of first pins which is mounted on a first surface of the substrate and each of which has a first connecting section and a first shaft section having a diameter smaller than that of the first connecting section;
      at least one first electronic component which is mounted on the first surface of the substrate and whose height is not larger than that of each of the first pins when being mounted;
      a first resin sealant configured to seal the first surface so as to expose an end face of the first shaft section opposite to where the first connecting section is provided;
      a plurality of second pins which is mounted on a second surface of the substrate and each of which has a second connecting section and a second shaft section having a diameter smaller than that of the second connecting section;
      at least one second electronic component which is mounted on the second surface of the substrate and whose height is not larger than that of each of the second pins when being mounted; and
      a second resin sealant configured to seal the second surface so as to expose an end face of the second shaft section opposite to where the second connecting section is provided,
   the image sensor chip includes:
      a light receiving unit configured to perform photoelectric conversion on an incident optical signal; and
      a back-surface electrode provided on a surface facing the light receiving unit by through-wiring, wherein
   the first shaft section exposed on the first resin sealant is connected to the back-surface electrode, and thereby the image sensor chip is connected to the mount assembly.

2. The imaging apparatus according to claim 1, further comprising a motherboard having a connection electrode, wherein
   the second shaft section exposed on the second resin sealant is connected to the connection electrode, and thereby the motherboard is connected to the mount assembly.

3. The imaging apparatus according to claim 1, further comprising a cable assembly in which a plurality of cables is fixed by a fixing member, wherein
   the second shaft section exposed on the second resin sealant is connected to a cable core exposed on a connection end face of the cable assembly, and thereby the cable assembly is connected to the mount assembly.

4. An endoscope apparatus comprising an insertion unit including the imaging apparatus according to claim 1 at a distal end of the insertion unit.

* * * * *